(12) United States Patent
Niggel et al.

(10) Patent No.: US 9,149,807 B2
(45) Date of Patent: Oct. 6, 2015

(54) SPECIMEN TEST UNIT

(75) Inventors: Brett Niggel, Corry, PA (US); Scott Jost, Glen Ellyn, IL (US)

(73) Assignees: Berlin Packaging, LLC, Chicago, IL (US); Teclab Inc., Blacksburg, VA (US)

( * ) Notice: Subject to any disclaimer, the term of this patent is extended or adjusted under 35 U.S.C. 154(b) by 511 days.

(21) Appl. No.: 13/589,326

(22) Filed: Aug. 20, 2012

(65) Prior Publication Data

US 2014/0051178 A1  Feb. 20, 2014

(51) Int. Cl.
| | |
|---|---|
| *G01N 33/50* | (2006.01) |
| *B01L 3/00* | (2006.01) |
| *A61B 10/00* | (2006.01) |
| *A61B 10/02* | (2006.01) |
| *A61F 13/38* | (2006.01) |
| *G01N 1/02* | (2006.01) |

(52) U.S. Cl.
CPC ........... *B01L 3/5029* (2013.01); *A61B 10/0045* (2013.01); *A61B 10/0096* (2013.01); *A61B 10/02* (2013.01); *A61F 13/38* (2013.01); *B01L 2300/042* (2013.01); *B01L 2300/047* (2013.01); *B01L 2300/049* (2013.01); *B01L 2300/0672* (2013.01); *B01L 2300/0832* (2013.01); *B01L 2400/0644* (2013.01); *B01L 2400/0683* (2013.01); *G01N 2001/028* (2013.01); *Y10T 436/25* (2015.01)

(58) Field of Classification Search
CPC ........................ B01L 3/5029; G01N 2001/028
See application file for complete search history.

(56) References Cited

U.S. PATENT DOCUMENTS

| | | | |
|---|---|---|---|
| 5,266,266 A | 11/1993 | Nason | |
| 6,248,294 B1 | 6/2001 | Nason | |
| 7,114,403 B2 | 10/2006 | Wu et al. | |
| 7,648,681 B2 | 1/2010 | Meyer et al. | |
| 7,871,568 B2 | 1/2011 | Liang et al. | |
| 2003/0143752 A1* | 7/2003 | Feldsine et al. | 436/164 |
| 2005/0106753 A1 | 5/2005 | Wu et al. | |
| 2009/0269246 A1 | 10/2009 | Hasegawa | |

* cited by examiner

*Primary Examiner* — Paul Hyun
(74) *Attorney, Agent, or Firm* — Adam K. Sacharoff; Much Shelist (57) ABSTRACT

A self-contained specimen testing unit consisting of a swab-tip with attached, hollow swab-stick, an outer, elongated, removable tube housing cover that surrounds and protects the swab-tip and swab-stick, a dropper removably secured to the end of the tube cover, a dropper cap, a piercing closure member, a rotatable base closure member coupled to the piercing closure element, a membrane member mounted in the base closure member, and reagent-solution storage container screwed onto the end of the rotatable base closure member and sealed by the membrane member thereof. A method of using the unit is also disclosed whereby the piercing unit pierces the membrane when reagent solution is to be delivered to the swab-tip.

16 Claims, 12 Drawing Sheets

FIG. 7D

SPECIMEN TEST UNIT

BACKGROUND OF THE INVENTION

The present invention is directed to a specimen test device that includes one integral unit containing all of the components necessary for delivering a biological test sample to a testing tray, or the like, for analysis. An example of such a unit is disclosed in U.S. Pat. No. 5,266,266, which unit includes a hollow cover tube or housing, a swab and hollow shaft for the swab mounted in the hollow tube, a removable cover for the swab, and a squeezable storage compartment for a reagent solution. The end of the hollow shaft for the swab extends into the interior of the storage container and is connected to a rod contained in the storage compartment via a scored or break-off section, whereby, when the hollow swab shaft is broken off from the rod via the break-off section, by bending the flexible storage compartment, reagent solution is free to flow through the hollow swab-shaft to the swab containing the collected biological sample, for reaction therewith. The reagent is forced to flow from the storage compartment through the hollow swab-shaft to the swab by squeezing the storage compartment.

The above-described prior-art product suffers for considerable disadvantages. Firstly, the breaking of the scored or break-off section by means of bending is difficult to achieve and oft-times requires more than one attempt. Secondly, such bending to make the break may occur by chance or accident, before the required time, which required time is after the specimen has been swabbed. Thirdly, the storage compartment is made part and parcel with the housing of the product, whereby the filling of the storage compartment via an aperture thereof with a specific reagent adds to the overall complexity of producing a finished product. The present invention overcomes the above-mentioned drawbacks and deficiencies of the prior art.

SUMMARY OF THE INVENTION

It is, therefore, the primary objective to provide a specimen test unit that overcomes the above-mentioned drawbacks of the prior-art devices. Toward this end, the self-contained, specimen testing unit consists of a swab-tip with attached, hollow swab-stick; an outer, elongated, removable housing or tube cover that surrounds and protects the swab-tip and swab-stick; a dropper removable secured to the end of the housing cover; a dropper cap ; a piercing closure member; a rotatable base closure member coupled to the piercing closure element; a membrane member mounted in the base closure member; and reagent-solution storage container screwed onto the end of the rotatable base closure member and sealed by the membrane member in the base closure member.

According to the method of using the self-contained, specimen testing unit, one first removes the swab-cover member and the housing cover, and exposing the swab-tip thereby. One then collects a sample to be assayed with the swab-tip, and then replaces the swab-cover member and the housing cover over the swab-tip and swab-shaft. Then, the membrane is pierced by means of the piercing closure member, allowing the reagent solution to flow out of the reagent storage container. The piercing is achieved by rotating the base closure member relative to the piercing closure member to cause a piercing tip to move toward the membrane mounted in the interior of the base closure member. This allows the reagent solution to flow through the piercing closure member and base closure member, through the swab-shaft to the swab-tip to react with the sample on the swab-tip. Thereafter, the dropper cap is removed and the storage container is squeezed to force the reacted solution out through the dropper to a surface for inspection.

BRIEF DESCRIPTION OF THE DRAWING

The invention will be more readily understood with reference to the accompanying drawings, wherein.

DETAILED DESCRIPTION OF THE INVENTION

Figure 1:
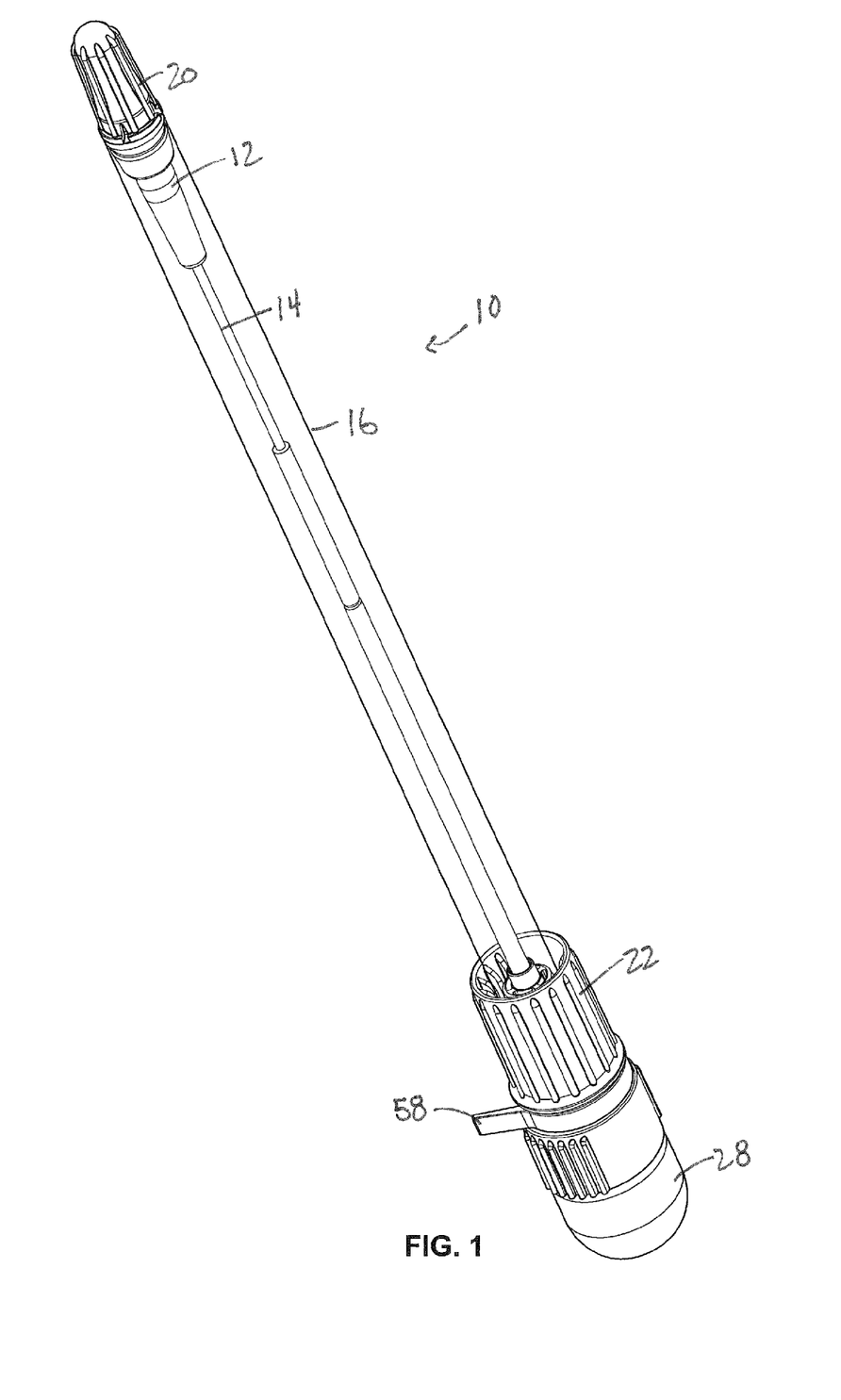
FIG. 1 is a perspective view of the specimen test unit of the invention.
Figure 2:
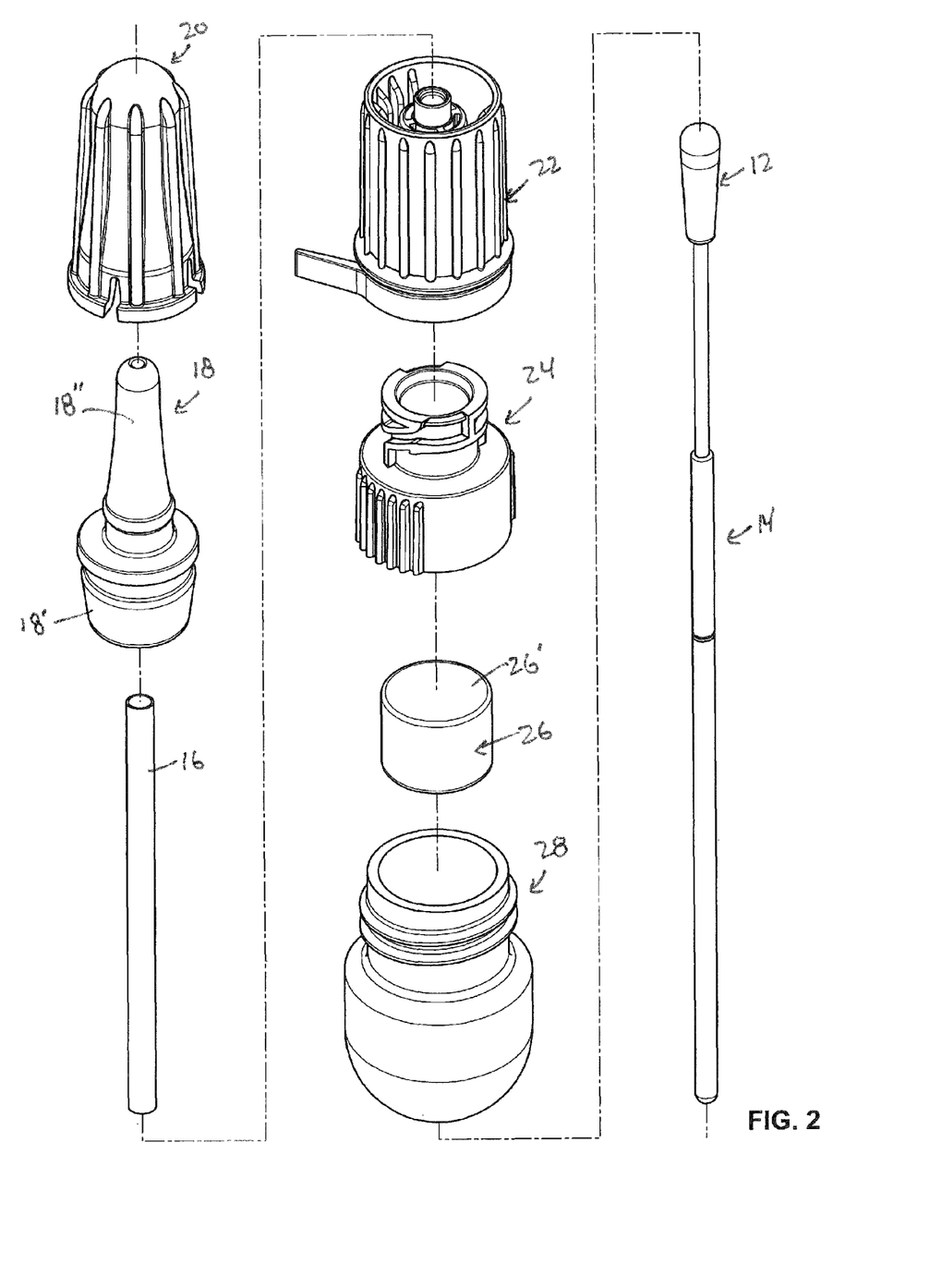
FIG. 2 is an assembly view, in perspective, of the specimen test unit of FIG. 1.
Figures 3A, 3B:
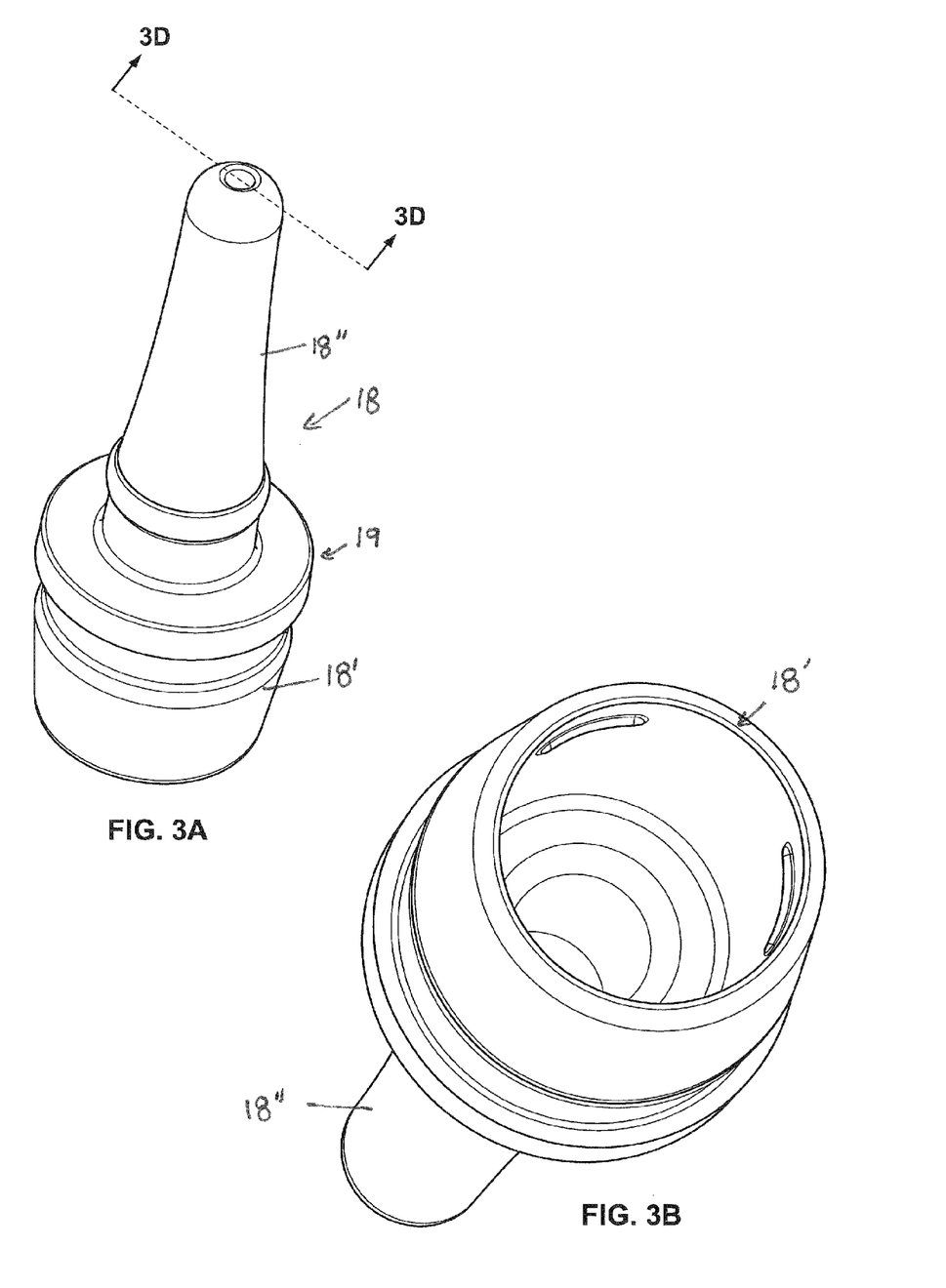
FIGS. 3A and 3B are isometric views of the dropper of the specimen test unit of FIG. 1.
Figure 3C:
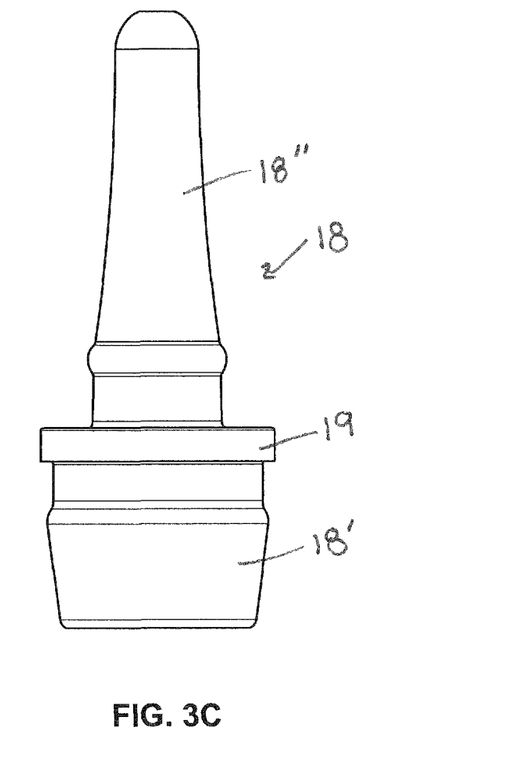
FIG. 3C is a side elevational view of the dropper of FIGS. 3A and 3B.
Figure 3D:
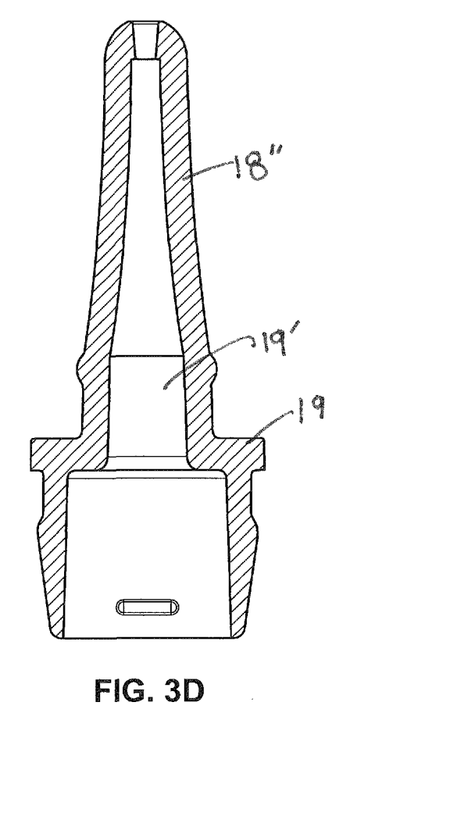
FIG. 3D is a cross-sectional view taken along line 3D-3D of FIG. 3A.
Figures 4A, 4B:
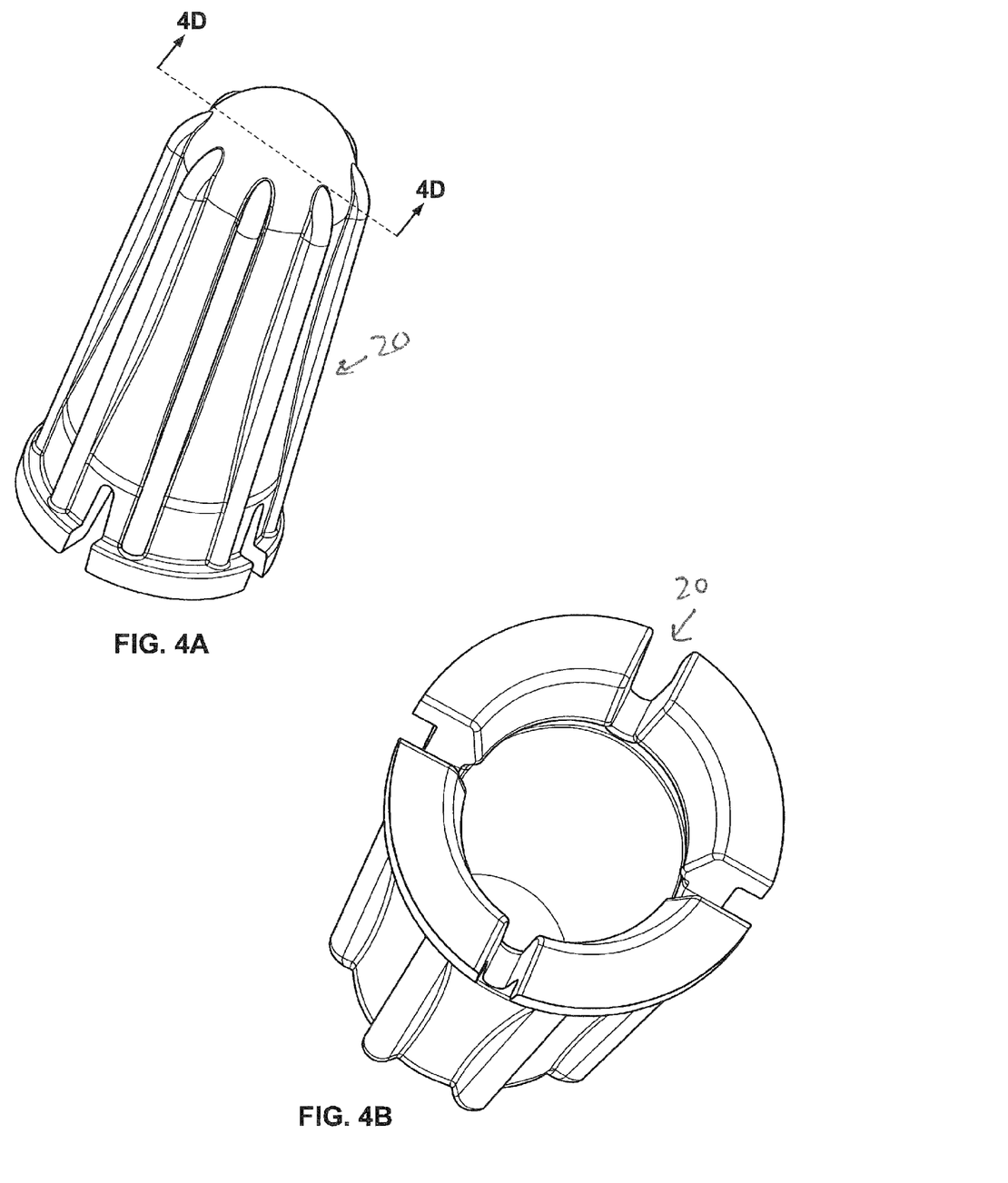
FIGS. 4A and 4B are isometric views of the removable tip cap of the dropper FIGS. 3A and 3B.
Figure 4C:
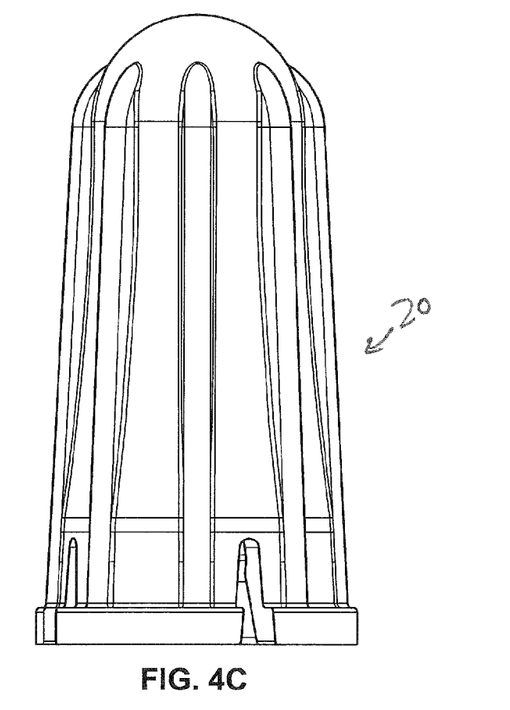
FIG. 4C is a side elevational view of the tip cap of FIGS. 4A and 4B.
Figure 4D:
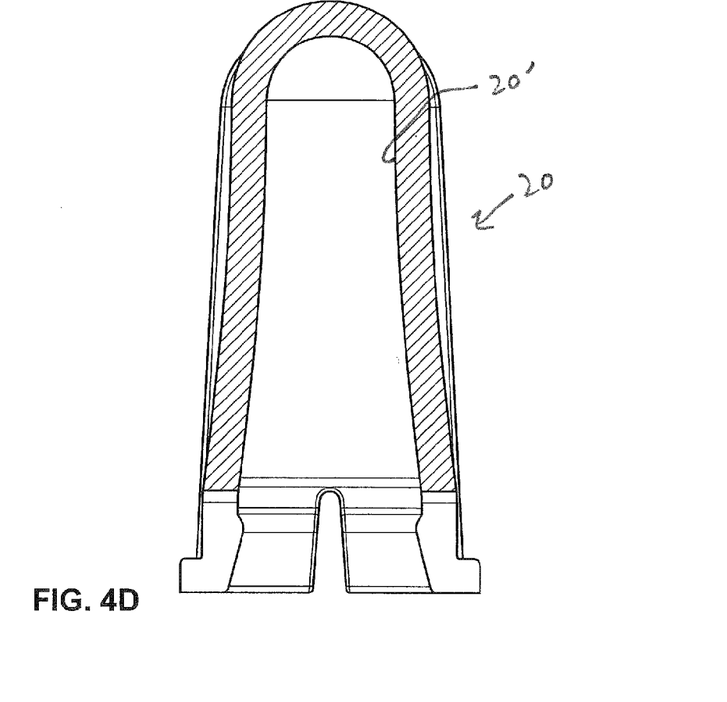
FIG. 4D is a cross-sectional view taken along line 4D-4D of FIG. 4A.
Figure 5A:
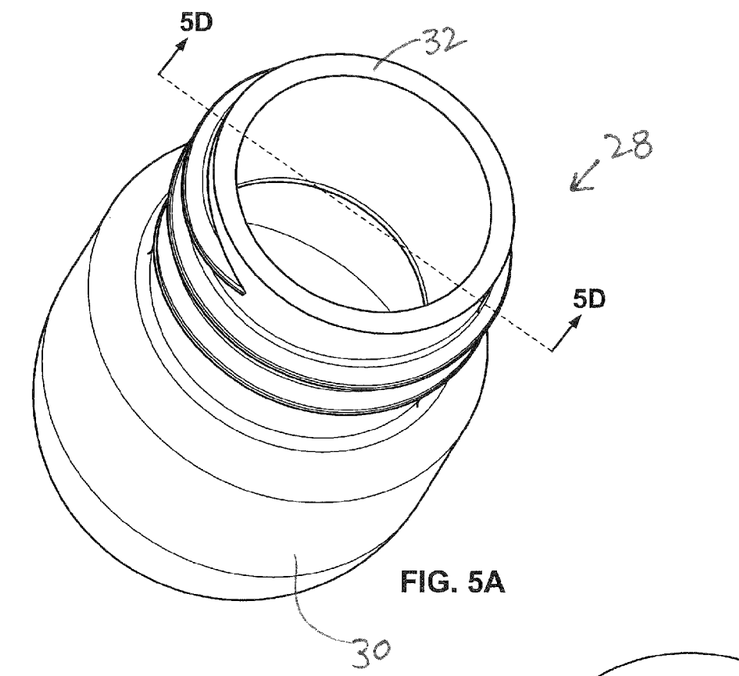
FIGS. 5A and 5B are isometric views of the storage container for reagent solution of the specimen test unit of FIG. 1
Figure 5B:
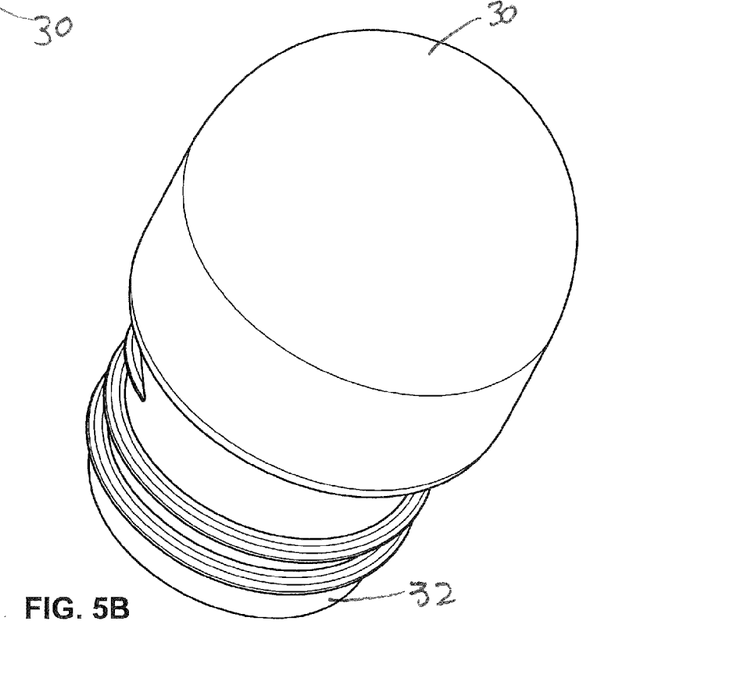
Figure 5C:
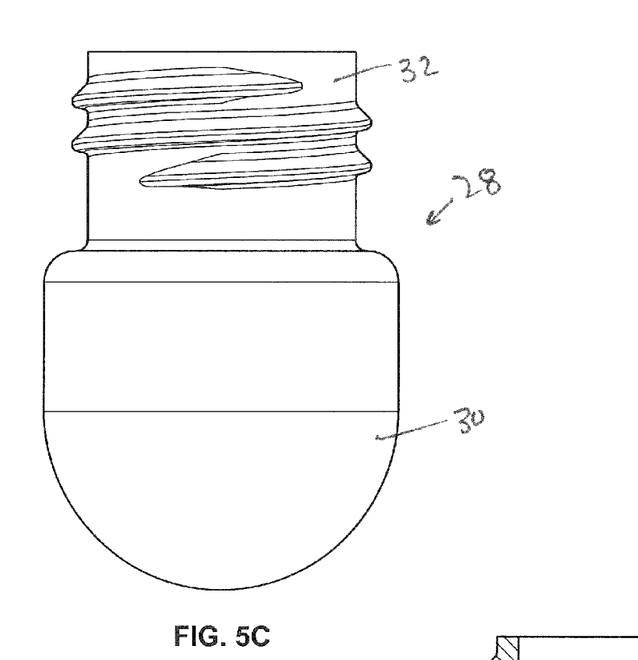
FIG. 5C is a side elevational view of the storage container for reagent solution of FIGS. 5A and 5B.
Figure 5D:
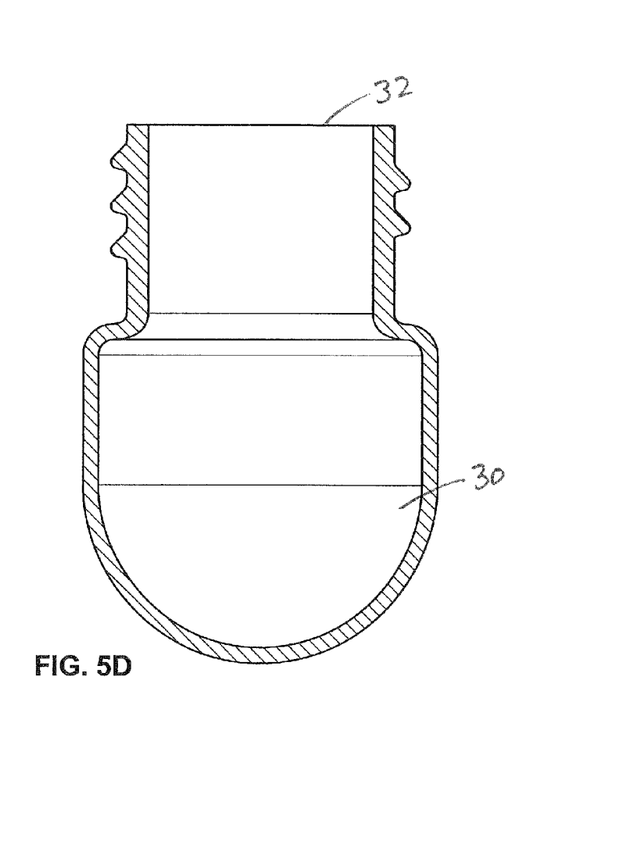
FIG. 5D is a cross-sectional view taken along line 5D-5D of FIG. 5A.

Referring now to the drawings in greater detail, and to FIGS. 1 and 2 for now, the self-contained, specimen test unit is indicated generally by reference numeral 10. The specimen test unit consists of the following elements: a swab-tip 12 with attached, hollow swab-stick 14; an outer, elongated, removable tube cover or housing 16 that surrounds and protects the swab-tip and swab-stick; a dropper 18 secured to the end of the tubular housing 16; a dropper cap 20; piercing closure element 22; rotatable base closure member 24 coupled to the piercing closure element; membrane member 26; and reagent-solution storage container 28 screwed onto the end of the rotatable base closure member 24.

Referring now to FIGS. 3A-3D, there is shown, in detail, the dropper 18. The dropper 18 is made of flexible material, such as low-density polypropylene. It consists of a main body portion 18' defining a hollow interior, for receiving therein the swab-tip 12. The main body portion 18' is telescopingly received in the end of the tube cover 16, with the circumferential seat 19 closing off the end of the tubular housing 16. Connected to the main body portion 18' is dispensing tip 18", which tip is used to dispense therethrough the biological sample with specific reagent solution onto a tray, or the like, for inspection, as described hereinbelow.

Referring now to FIGS. 4A-4D, there is shown dropper cap 20 made of non-flexible polypropylene. The dropper cap 20 defines a hollow interior for sliding over the dropper dispensing tip 18". A tapered interior 20' provides a snug fit between it and the exterior of the dropper dispensing tip 18". The dispensing tip 18" of the dropper 18 and dropper cap 20 protrude from the end of the tube cover 16.

Referring now to FIGS. 5A-5D, there is shown, in detail, the reagent-solution storage container 28, which may typically be three ml. in volume. The reagent-solution storage container 28 is made of flexible material, such as low-density polypropylene, and includes a main storage compartment or section 30, and a narrower, mounting section 32 provided with exterior threads for threaded engagement with mating threads formed in the interior surface of the rotatable base closure member 24 described hereinbelow in greater detail. The separate and separable storage container 28 allows for such to be purchased independently of the manufacture of the specimen unit 10, allowing different reagent solutions to be coupled to a standardized specimen unit comprised of the rest of the components thereof besides the storage compartment, or to be filled independently with the specific assaying reagent.

Figure 6A:
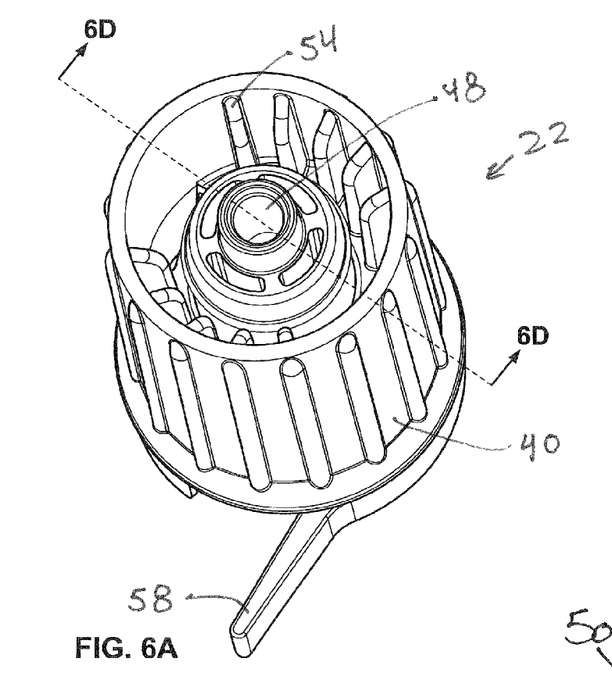
FIGS. 6A and 6B are isometric views of the piercing closure element of the specimen test unit of FIG. 1.
Figure 6B:
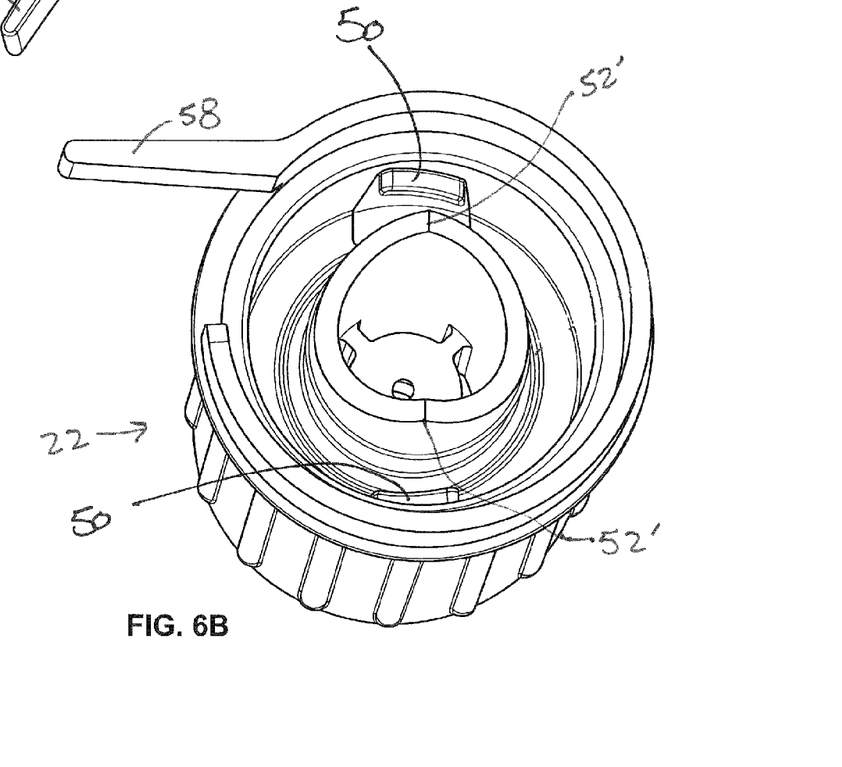
Figure 6C:
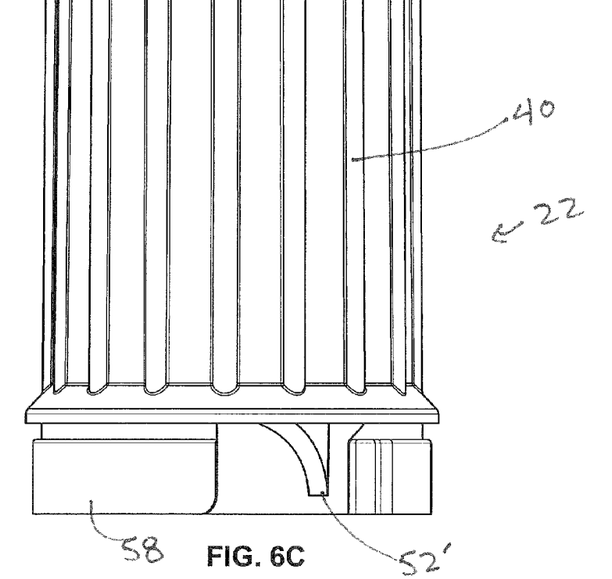
FIG. 6C is a side elevational view of the piercing closure element of FIGS. 6A and 6B.
Figure 6D:
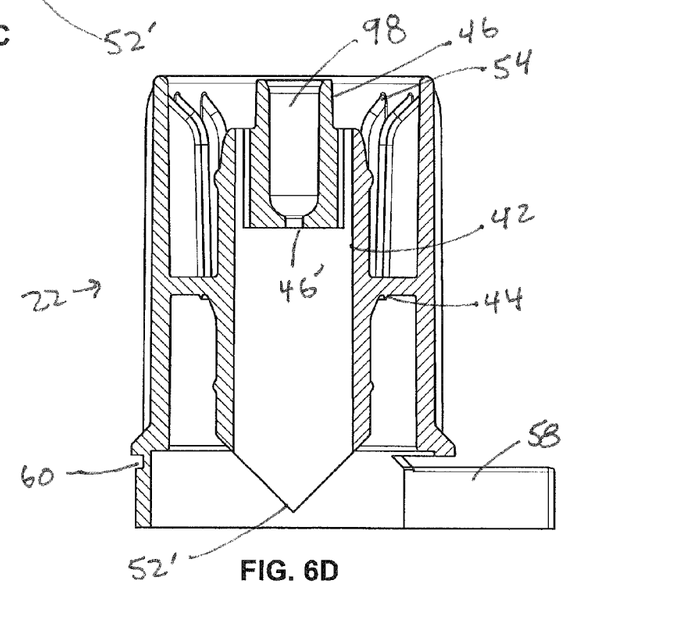
FIG. 6D is a cross-sectional view taken along line 6D-6D of FIG. 6A.
Figure 7A:
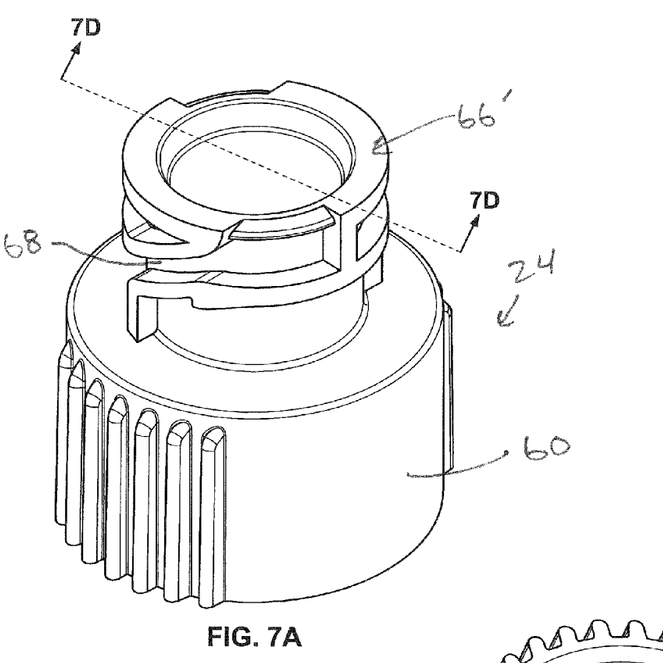
FIGS. 7A and 7B are isometric views of the base closure element that mounts both the storage container of FIGS. 5A and 5B and the piercing closure element of FIGS. 6A and 6B.
Figure 7B:
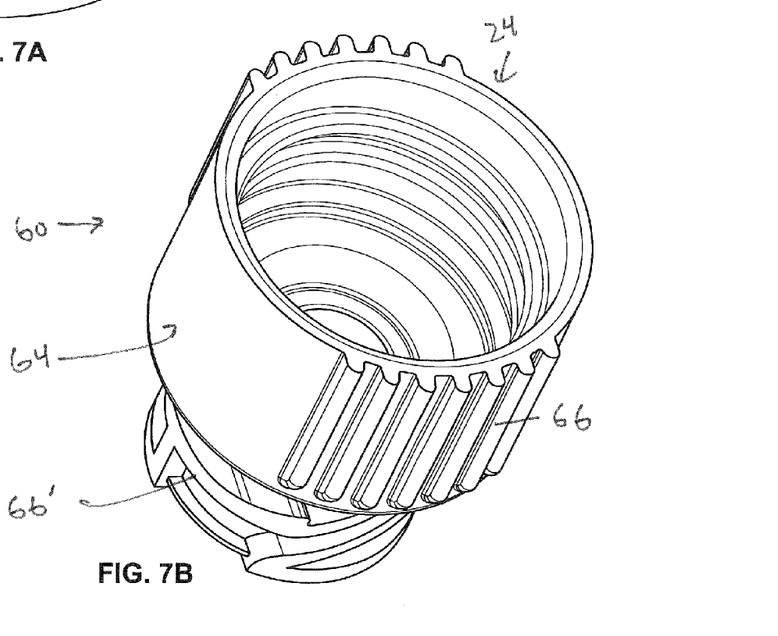
Figure 7C:
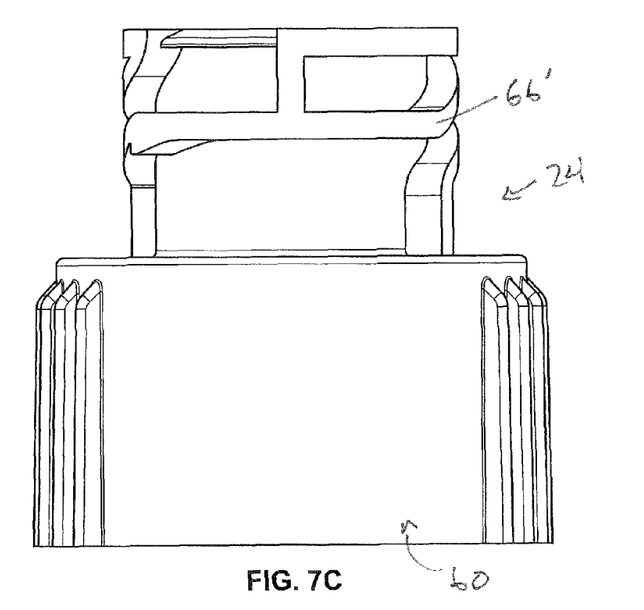
FIG. 7C is a side elevational view of the base closure element of FIGS. 7A and 7B.
Figure 7D:
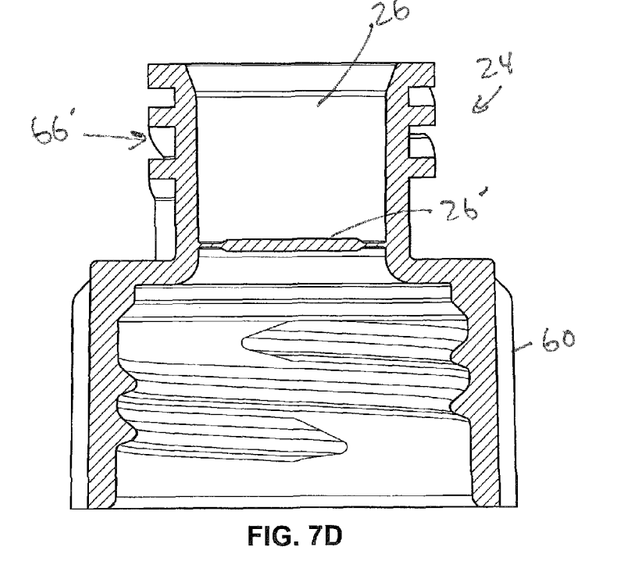
FIG. 7D is a cross-sectional view taken along line 7D-7D of FIG. 7A.

Referring now to FIGS. 6A-6, there is shown, in detail, the piercing closure member 22, made of non-flexible polypropylene, for example. The piercing closure member 22 consists of a main housing 40 defining a hollow interior. Concentrically mounted in the hollow interior of the housing 40 is a central section 42 mounted to the interior wall surface of the housing 40 via annular mounting ring or rib 44. The central section 42 has a hollow mounting sleeve 46 formed integral therewith defining a central opening 48 for receiving and slidingly-removably mounting therein the end of the swab-stick 14. The mounting sleeve 46 has a through-opening 46' that fluidly communicates with the hollow interior of the central section 42, whereby reagent solution emanating from the reagent-solution storage container 28 is allowed to pass through the hollow interior of the swab-stick 14 and to the swab-tip 12 after the swab-tip has been used to collect a biological sample, as described hereinbelow in greater detail. The interior surface of the annular wall of the main housing 40 is provided with male lugs 50, which mate with corresponding female lugs thereat of the rotatable base closure member 24. Projecting downwardly from, and integral with, the central section 42 is a piercing element 52, which terminates in a pair of piercing tips or nibs 52', which are used to pierce through the membrane 26 contained in the storage container 28, when the rotatable base closure member 24 is rotated, as described hereinbelow. The piercing tips 52' project below the bottom-edge of the main housing 40.

Provided in the interior of the housing 40, integrally connected to, and projecting interiorly from, the inner surface of the annular wall of the housing 40, are a plurality of fins or brackets 54. Each fin extends interiorly toward the central section 42, with the distal tips or faces of the fins or brackets being spaced from the outer wall of the central section 42, whereby there is provided an annular opening defined between the tips of the fins 54 and the outer wall of the central section 42 in which is slidingly received the end of the tube or housing cover 16, whereby a tight, forced-fit connection is provided.

The piercing closure member 22 is provided with sealing closure strip or tab 58, in the conventional manner, which seals the rotatable base closure member 24 and the piercing closure member 22 and prevents relative rotation therebetween until the strip 58 has been removed. The strip 58 is attached to the bottom edge-surface of the housing 40 via a connecting web 60. The strip 58 attached, covers over the piercing tips 52', and exposes them when removed. The outer wall surface of the housing 40 is provided with a knurled surface to aid in gripping.

Referring now to FIGS. 7A-7D, there is shown, in detail, the rotatable base closure member 24. The rotatable base closure member 24 consists of a main body portion 64 defining a hollow interior, and an outer knurled surface 66 for aiding in the gripping thereof. Projecting forwardly from the main body portion is smaller-diameter, hollow threaded mounting section 66' defining exterior female threads 68 for mating with the cooperating interior male threads of the main housing 40 of the piercing closure member 22. The hollow threaded mounting section 66 is received in the bottom hollow interior of the housing 40 of the piercing closure member 22, and prevented from relative rotation therewith until the sealing closure strip or ribbon 58 has been removed. Mounted in the interior of the hollow mounting section 66' is the membrane housing or sleeve 26, which defines a flexible membrane surface 26' made of conventional material, that, when pierced by the piercing closure element 22, allows the reagent solution to travel from the storage compartment, through the interior of the rotatable base closure member 24, the interior of the piercing closure element 22, and then trough the interior of the swab-stick or shaft 14, as described hereinbelow in greater detail. The flexible membrane surface 26 seals the main storage compartment.

The following is a description of how the specimen test unit 10 is used. One first removes the dropper cap 20 and the dropper 18, and then the tube or housing cover 16, thus exposing the swab-tip 12 and its stick or shaft 14. One grips either the piercing closure member 22 or the rotatable base closure member 24, where it thereby serves as a handle for the swab-stick 14, whereupon one then inserts the swab-tip 12 into a biological sample to be assayed. After having retrieved the sample, the cover tube 16, the dropper 20, the dropper cap 20 are re-attached to thus enclose swab-tip with sample thereby. Then, one tears off the sealing closure strip or tab 58, which exposes the piercing tips 52'. One then grips the knurled section of the piercing closure member 22 with one hand, and then grips the knurled section of the rotatable base closure member 24 with the other hand, and then rotates the rotatable base closure member 24 relative to the piercing closure member 22. Preventing the rotation of the piercing closure member by the hand grasped thereat, the rotation of the rotatable base closure member 24 causes translational movement of the piercing closure member 22 relative to the rotatable base closure member 24, until such point that the piercing tips or prongs 52' pierce the membrane 26', allowing the reagent solution to flow out therefrom. By orienting the unit such that the swab-tip is positioned in a downward position, the liquid reagent flows from the interior of the storage container 28, through the hollow interior of the main body portion 64 and interiorly through the smaller-diameter, hollow threaded mounting section 66', and then interiorly trough the central section 42 of the piercing closure member 22 and interiorly through the hollow mounting sleeve 46 via the aperture 46' thereof, for entry and passage through the hollow swab-stick or swab-stick 14 for wetting the swab-tip 12 and mixing with the biological sample stored on the swab-tip. At this point, the dropper cap 20 is removed again, and the reacted liquid solution is allowed to exit the unit via the exit of the dropper 18. At any point during passage of the reagent solution, the storage container 28 may be squeezed to force the more reagent out of the container, or to force the reagent through the device, or to force the reacted biological solution out through the dropper, to a slide or tray, for visual inspection of the color of the reacted solution, in order to determine the state of the assay, whether positive or negative. The dropper 18 is, also, preferably provided with a filter 19' (FIG. 3D) for filtering out the biological sample-remains.

While a specific embodiment of the invention has been shown and described, it is to be understood that numerous changes and modifications may be made therein without departing from the scope and spirit of the invention as set forth in the appended claims. While it has been shown and disclosed that the coupling between the piercing closure member 22 and the base closure member 24 are threads allowing relative rotation therebetween, other couplers may be used that allow translational movement of the piercing closure member 22 relative to the base closure member 24 may be employed. Also, while the device has been shown having a swab-tip for use in collecting the sample, other collectors may be used depending upon the specific end-use.

What is claimed is:

1. In a specimen testing unit comprising a sample-collecting element having a sample-collecting tip and a hollow sample-collecting shaft to the end of which is secured said sample-collecting tip, an elongated, hollow, tubular housing in which is received said sample-collecting element, a removable cover member for covering over said sample-collecting tip when not in use, a reagent storage container filled with reagent solution specific to a biological specimen to be assayed, and an actuator device for breaking a seal of the reagent storage container to allow the reagent solution to flow therepast and through said sample-collecting shaft to said sample-collecting tip after said cover element and said elongated, tubular housing had, firstly, been removed to expose said sample-collecting tip for retrieving a biological sample to be assayed, and then, secondly, after they have been reattached, the improvement comprising:

said actuator device comprising a piercing closure member having at least one piercing tip;

a base closure member coupled to said piercing closure member;

said piercing closure member comprising a first cooperating element, and said base closure member comprising a second cooperating element and a third cooperating element, said first and second cooperating elements mounting said piercing closure member for selected translational movement toward said base closure member to bring said at least one piercing tip into the interior of said base closure member; and said reagent storage container comprising a fourth cooperating element for removable mounting to said third cooperating element of said base closure member; and a membrane element comprising a membrane for sealing said reagent storage container, said membrane being pierced through by said at least one piercing tip when said piercing closure member is translated toward said base closure member, whereby the reagent solution in said reagent storage container is allowed to flow out therefrom, through said actuator device, and through said swab-shaft to deliver the reagent solution to said sample-collecting-tip after said sample-collecting tip had collected a biological sample to be assayed.

2. The specimen testing unit according to claim 1, wherein said piercing closure member comprises a main housing defining an interior wall surface; and an interior, hollow central section mounted in said main housing defining an outer wall surface; said first cooperating element being located on the interior wall surface of said main housing;

said sample-collecting element being a swab-element, said sample-collecting tip comprising a swab-tip, and said sample-collecting shaft being a swab-shaft;

said central section comprising central passageway for receiving therein the end of said swab-shaft; and said main housing further comprising a plurality of filler dements for partially filling the space between said outer wall surface of said central section and said inner wall surface of said main housing, thereby defining an annular space therebetween in which is mounted the end of said elongated tubular housing.

3. The specimen testing unit according to claim 2, wherein said main housing comprises a lower edge surface, and further comprises a sealing ribbon mounted to said lower edge surface for preventing relative movement between said piercing closure member and said base closure member until the time said membrane element is to be pierced by said at least one piercing tip.

4. The specimen testing unit according to claim 3, wherein at least one piercing tip projects below said lower edge surface, and is exposed after said sealing ribbon has been torn away, to thus allow relative movement between said piercing closure member and said base closure member; each of said cooperating elements comprising respective mating threads.

5. The specimen testing unit according to claim 3, wherein the base closure member comprises a hollow main body portion defining an interior wall surface, said third cooperating element being located on said interior wall for mating with said fourth cooperating element of said reagent storage container; said base closure member further comprising a first hollow mounting section defining a wall surface on which is mounted said second cooperating element for engagement with said first cooperating element of said piercing closure member.

6. The specimen testing unit according to claim 5, wherein each of said cooperating elements comprises respective mating threads, and said membrane element being mounted in said first hollow mounting section of said base closure member, such that when the base closure member is attached to the reagent storage container the membrane seals the reagent storage container.

7. The specimen testing unit according to claim 5, wherein said reagent storage container comprises a main storage compartment for storing reagent solution, and a second hollow mounting section defining an annular surface on which is mounted said fourth cooperating element for mating with said third cooperating element of said base closure member.

8. The specimen testing unit according to claim 5, wherein said reagent storage container comprises a main storage compartment for storing reagent solution, and a second hollow mounting section defining an annular surface connected to said main storage compartment.

9. The specimen testing unit according to claim 1, wherein the base closure member comprises a hollow main body portion defining an interior wall surface, said third cooperating element being located on said interior wall for mating with said fourth cooperating element of said reagent storage container; and said base closure member further comprising a first hollow mounting section defining a wall surface on which is mounted said second cooperating element for engagement with said first cooperating element of said piercing closure member; said membrane element being mounted in said first hollow mounting section of said base closure member and comprising a sleeve portion to mount the membrane thereto, and wherein when the base closure member is attached to the reagent storage container, whereby said membrane sealing the reagent storage container until pierced by said at least one piercing tip.

10. The specimen testing unit according to claim 9, wherein said reagent storage container comprises a main storage compartment for storing reagent solution; and a second hollow mounting section defining an annular surface on which is mounted said fourth cooperating element for mating with said third cooperating element of said base closure member.

11. The specimen testing unit according to claim 9, wherein said piercing closure member comprises a main housing defining an interior wall surface; an interior, hollow central section mounted in said main housing defining an outer wall surface, said first cooperating element being located on the interior wall surface of said main housing;
   said sample-collecting element being a swab-element, said sample-collecting tip comprising a swab-tip, and said sample-collecting shaft being a swab-shaft;
   said central section comprising central passageway for receiving therein the end of said swab-shaft; and
   said main housing further comprising a plurality of filler elements for partially filling the space between said outer wall surface of said central section and said inner wall surface of said main housing, thereby defining an annular space therebetween in which is mounted the end of said elongated tubular housing.

12. The specimen testing unit according to claim 11, wherein said main housing comprises a lower edge surface, and further comprises a sealing ribbon mounted to said lower edge surface for preventing relative movement between said piercing closure member and said base closure member until the time said membrane element is to be pierced by said at least one piercing tip.

13. The specimen testing unit according to claim 1, wherein said reagent storage container comprises a main storage compartment for storing reagent solution, and a second hollow mounting section defining an annular surface on which is mounted said fourth cooperating element for mating with said third cooperating element of said base closure member.

14. A specimen testing unit comprising:
   a swab-element having a swab-tip and a hollow swab-shaft to the end of which is secured said swab-tip;
   an elongated, hollow, housing cover in which is received said swab-element;
   a removable swab-cover member for covering over said swab-tip when not in use;
   a reagent storage container filled with reagent solution specific to a biological specimen to be assayed;
   and an actuator device for breaking a seal of said reagent storage container for allowing said reagent solution to flow therepast and through said swab-shaft to said swab-tip after said swab-cover element and said elongated, hollow, housing cover had, firstly, been removed to expose said swab-tip for retrieving a biological sample to be assayed and then, secondly, after they have been reattached:
   said actuator device comprising a piercing closure member having at least one piercing tip for piercing the seal of said reagent storage container;
   a base closure member coupled to said piercing closure member;
   said piercing closure member comprising a first cooperating element, and said base closure member comprising a second cooperating element and a third cooperating element, said first and second cooperating elements mounting said piercing closure member for selected translational movement toward said base closure member to bring said at least one piercing tip into the interior of said base closure member; and
   said reagent storage container comprising a fourth cooperating element for removable mounting said reagent storage container to said third cooperating element of said base closure member; and
   a membrane element comprising a membrane for sealing said reagent storage container, said membrane being pierced through by said at least one piercing tip when said piercing closure member is translated toward said base closure member, whereby the reagent solution in said reagent storage container is allowed to flow out therefrom, through said actuator device, and through said swab-shaft to deliver the reagent solution to said swab-tip after said swab-tip had collected a biological sample to be assayed.

15. The specimen testing unit according to claim 14, wherein said base closure member comprises a hollow mounting section defining a wall surface on which is mounted said second cooperating element for engagement with said first cooperating element of said piercing closure member; said membrane element being mounted in said hollow mounting section and comprising a sleeve portion to mount the membrane thereto, and wherein when the base closure member is attached to the reagent storage container, whereby said membrane seals the reagent storage container until pierced by said at least one piercing tip.

16. The specimen testing unit according to claim 14, wherein said removable swab-cover member comprises a dropper member and a cover element for removable mounting over said dropper member, said dropper member being used to dispense the reacted solution of sample and reagent for inspection.

\* \* \* \* \*